US006757418B2

United States Patent
Wei et al.

(10) Patent No.: US 6,757,418 B2
(45) Date of Patent: Jun. 29, 2004

(54) METHOD AND SYSTEM FOR AUTOMATIC COMPUTED RADIOGRAPHY (CR) IMAGE COMPOSITION BY WHITE BAND DETECTION AND CONSISTENCY RECHECKING

(75) Inventors: Guo-Qing Wei, Plainsboro, NJ (US); Zhenyu Wu, Plainsboro, NJ (US); Jianzhong Qian, Princeton, NJ (US); Helmut Schramm, Neunkirchen (DE)

(73) Assignee: Siemens Corporate Research, Inc., Princeton, NJ (US)

( * ) Notice: Subject to any disclaimer, the term of this patent is extended or adjusted under 35 U.S.C. 154(b) by 456 days.

(21) Appl. No.: 09/855,956

(22) Filed: May 15, 2001

(65) Prior Publication Data

US 2002/0044676 A1 Apr. 18, 2002

Related U.S. Application Data

(60) Provisional application No. 60/230,773, filed on Sep. 7, 2000.

(51) Int. Cl.$^7$ ................................................. G06K 9/00
(52) U.S. Cl. ............................ 382/132; 378/4; 378/19; 378/62
(58) Field of Search ................................. 382/128, 129, 382/130, 131, 132, 133, 134, 150, 164, 170, 173, 199, 254, 255, 256; 378/4, 18, 37, 50, 53, 57, 62, 70, 146, 157, 196, 207; 600/407, 474, 457

(56) References Cited

U.S. PATENT DOCUMENTS

| 4,956,859 | A | * | 9/1990 | Lanza et al. ................. 378/157 |
| 5,539,838 | A | * | 7/1996 | Shimura ...................... 382/128 |
| 5,557,687 | A | * | 9/1996 | Hara ........................... 382/132 |
| 5,901,240 | A | * | 5/1999 | Luo et al. .................... 382/132 |
| 6,157,698 | A | * | 12/2000 | Pietikainen et al. .......... 378/58 |
| 6,212,291 | B1 | * | 4/2001 | Wang et al. ................. 382/132 |

* cited by examiner

Primary Examiner—Jayanti K. Patel
Assistant Examiner—Abolfazl Tabatabai
(74) Attorney, Agent, or Firm—Donald B. Paschburg; F. Chau & Associates, LLP

(57) ABSTRACT

A method for automatic CR image composition includes the following steps for each image in a CR image pair. A vertical gradient image is projected onto a y-axis to obtain a y-axis projection. Edge positions (candidates) are identified from white band edge positions based on an absolute maximum value of the y-axis projection. An intensity change constancy identifies candidates having orientation angles less than a threshold angle with respect to a horizontal. An intensity change value verifies intensity value differences on two candidate sides. A cross-correlation score is computed for the candidates having an error value below a threshold for the intensity change constancy and the intensity change value, by comparing a consistency of the candidates against image data of the CR image pair. A final overlap is identified for the CR image pair, based upon the cross-correlation score.

26 Claims, 6 Drawing Sheets

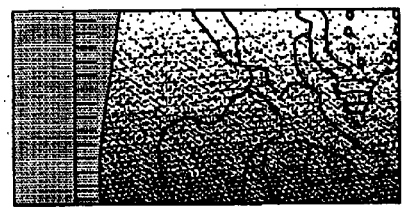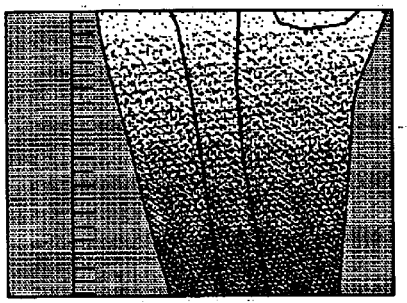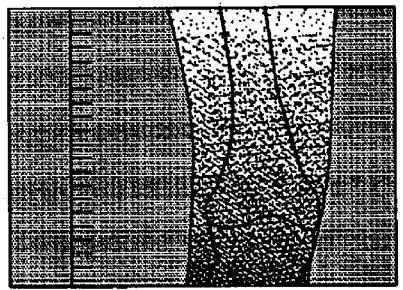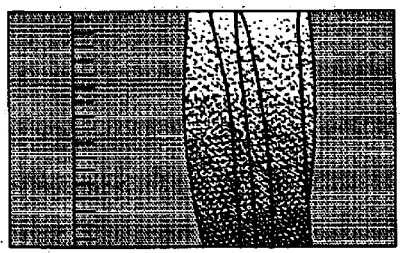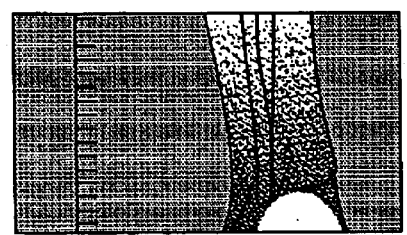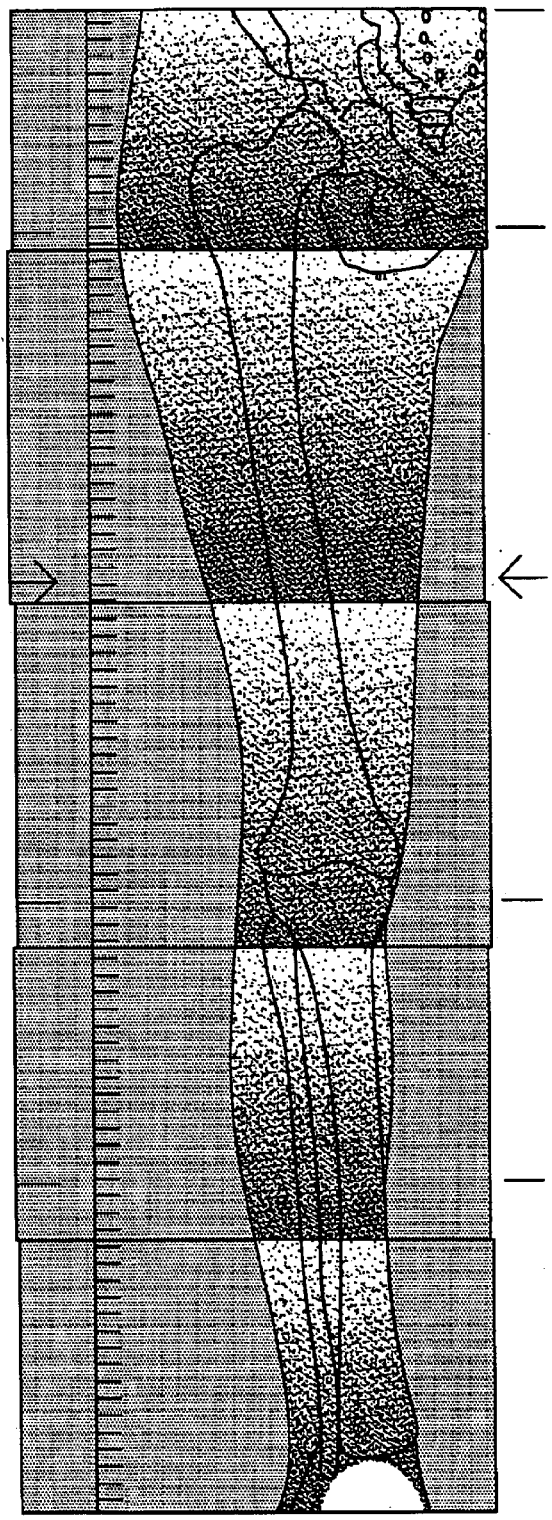
FIG. 7A                    FIG. 7B

METHOD AND SYSTEM FOR AUTOMATIC COMPUTED RADIOGRAPHY (CR) IMAGE COMPOSITION BY WHITE BAND DETECTION AND CONSISTENCY RECHECKING

CROSS-REFERENCE TO RELATED APPLICATIONS

This is a non-provisional application claiming the benefit of provisional application Ser. No. 60/230,773, filed on Sep. 7, 2000, the disclosure of which is incorporated herein by reference.

BACKGROUND

1. Technical Field

The present invention generally relates to image composing and, in particular, to a method and system for automatic Computed Radiography (CR) image composition by white band detection and consistency rechecking.

2. Background Description

In a new type of X-ray image acquisition referred to as Computed Radiography (CR), cassettes containing storage phosphor plates are placed one after another so that anatomy larger than the size of the plates can be imaged by stitching individual images together. Since all the images are acquired at the same time, there is no content difference in the overlap region of neighboring image plates. This is not the case in auto-stepping, where the acquisition device moves stepwise after each acquisition of a small image. In general, when auto-stepping is employed, distortions exist in overlap regions due to depth differences. FIG. 1 is a diagram illustrating a simplified view of a Computed Radiography (CR) image acquisition, according to the prior art.

Since individual images are digitized separately, there is a need to seamlessly combine the individual images after digitization. While such composition could be performed manually, manual approaches to composition are undesirably labor-intensive. Existing automatic methods that are based solely on cross correlation do not operate reliably, since the overlap between successive images is usually very small.

Accordingly, it would be desirable and highly advantageous to have a method and system for accurately and automatically combining Computed Radiography (CR) individual images after digitization.

SUMMARY OF THE INVENTION

The problems stated above, as well as other related problems of the prior art, are solved by the present invention, a method and system for automatic Computed Radiography (CR) image composition by white band detection and consistency rechecking.

The present invention provides a method and system for detecting the overlap region of successive images so that a mosaic of the images can obtained automatically and accurately.

According to an aspect of the invention, there is provided a method for automatic Computed Radiography (CR) image composition by white band detection and consistency rechecking. The method includes the step of receiving an original CR image pair for composition. For each image in the original CR image pair, the following steps are performed. A horizontal gradient image and a vertical gradient image are generated. The vertical gradient image is projected onto a y-axis of the each image to obtain a y-axis projection. Candidate edge positions are identified from among at least two white band edge positions according to a relative value of each of the at least two white band edge positions with respect to a percentage value of an absolute maximum value of the y-axis projection. An intensity change constancy of the candidate edge positions is determined to identify the candidate edge positions having orientation angles less than a pre-defined threshold angle with respect to a horizontal. The orientation angles are orthogonal with respect to angles of maximum intensity change for pixels on the candidate edge positions. An intensity change value is determined to verify intensity value differences on two sides of the candidate edge positions with respect to predefined criteria. An error function is defined to respectively obtain an error value for each of the candidate edge positions with respect to the intensity change constancy and the intensity change value. The candidate edge positions having the error value below a pre-specified threshold are selected. A cross-correlation score is computed for the selected candidate edge positions, by comparing a consistency of the selected candidate edge positions against image data corresponding to the original image pair. A final overlap is identified for the original image pair, based upon the cross-correlation score.

According to another aspect of the invention, I (x,y) represents the each image in the original CR image pair. $I_x$ (x,y) and $I_y$ (x,y) respectively represent the horizontal gradient image and the vertical gradient image. The y-axis projection is equal to $$P(y) = \sum_x I_y(x, y).$$

According to yet another aspect of the invention, the absolute maximum value of the y-axis projection is equal to $$\text{Max\_Py} = \max_y |P(y)|.$$

According to still yet another aspect of the invention, $\Omega = \{c | c=1,2, \ldots, N_c\}$ represents a set of indices for the candidate edge positions having y-coordinates at $\{y_c | c=1,2, \ldots, N_c\}$ in the each image. The angles of maximum intensity change for the pixels on a candidate edge position c from among the candidate edge positions are $R_c(x) = \arctan(I_y(x,y_c), I_x(x,y_c))$; $x \in D_c, c \in \Omega$, where $D_c$ is a set of points having a vertical gradient that is non-zero.

According to a further aspect of the invention, the set of points $D_c$ is used to exclude over-saturated and under-exposed pixels.

According to a still further aspect of the invention, an orthogonal angle to $R_c(x)$ is $R^{\perp}_c(x)$. An average angle of $R^{\perp}_c(x)$ represents an orientation angle of the candidate edge position c, and is equal to $A_c$, $$A_c = \sum_{x \in D_c} R^{\perp}_c(x) / |D_c|.$$

$|D_c|$ is a number of elements in the set of points $D_c$.

According to an additional aspect of the invention, the method further includes the step of excluding any of the candidate edge positions having an average angle below a pre-determined threshold from further consideration.

According to yet an additional aspect of the invention, the step of determining the intensity change constancy includes the following steps, performed for each of the candidate edge positions. A direction of maximum intensity change is determined for each of pixels on the each of the candidate edge positions. An orthogonal angle with respect to the direction of maximum intensity change is determined. A deviation is calculated of an orientation angle, measured as an average angle of the orthogonal angle, from the horizontal. The candidate edge positions having the deviation less than the pre-defined threshold are identified.

According to still yet an additional aspect of the invention, the step of determining the intensity change value includes the steps of measuring a relative intensity change across a candidate edge position c at two different, pre-defined offset values, and verifying that the relative intensity change satisfies the pre-defined criteria.

These and other aspects, features and advantages of the present invention will become apparent from the following detailed description of preferred embodiments, which is to be read in connection with the accompanying drawings.

BRIEF DESCRIPTION OF THE DRAWINGS

FIGS. 7A and 7B are diagrams illustrating an example of mosaic composition from 5 individual images, according to an illustrative embodiment of the present invention.

DETAILED DESCRIPTION OF PREFERRED EMBODIMENTS

The present invention is directed to a method and system for automatic Computed Radiography (CR) image composition by white band detection and consistency rechecking.

It is to be understood that the present invention may be implemented in various forms of hardware, software, firmware, special purpose processors, or a combination thereof. Preferably, the present invention is implemented as a combination of hardware and software. Moreover, the software is preferably implemented as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying Figures are preferably implemented in software, the actual connections between the system components (or the process steps) may differ depending upon the manner in which the present invention is programmed. Given the teachings herein, one of ordinary skill in the related art will be able to contemplate these and similar implementations or configurations of the present invention.

Figure 2:
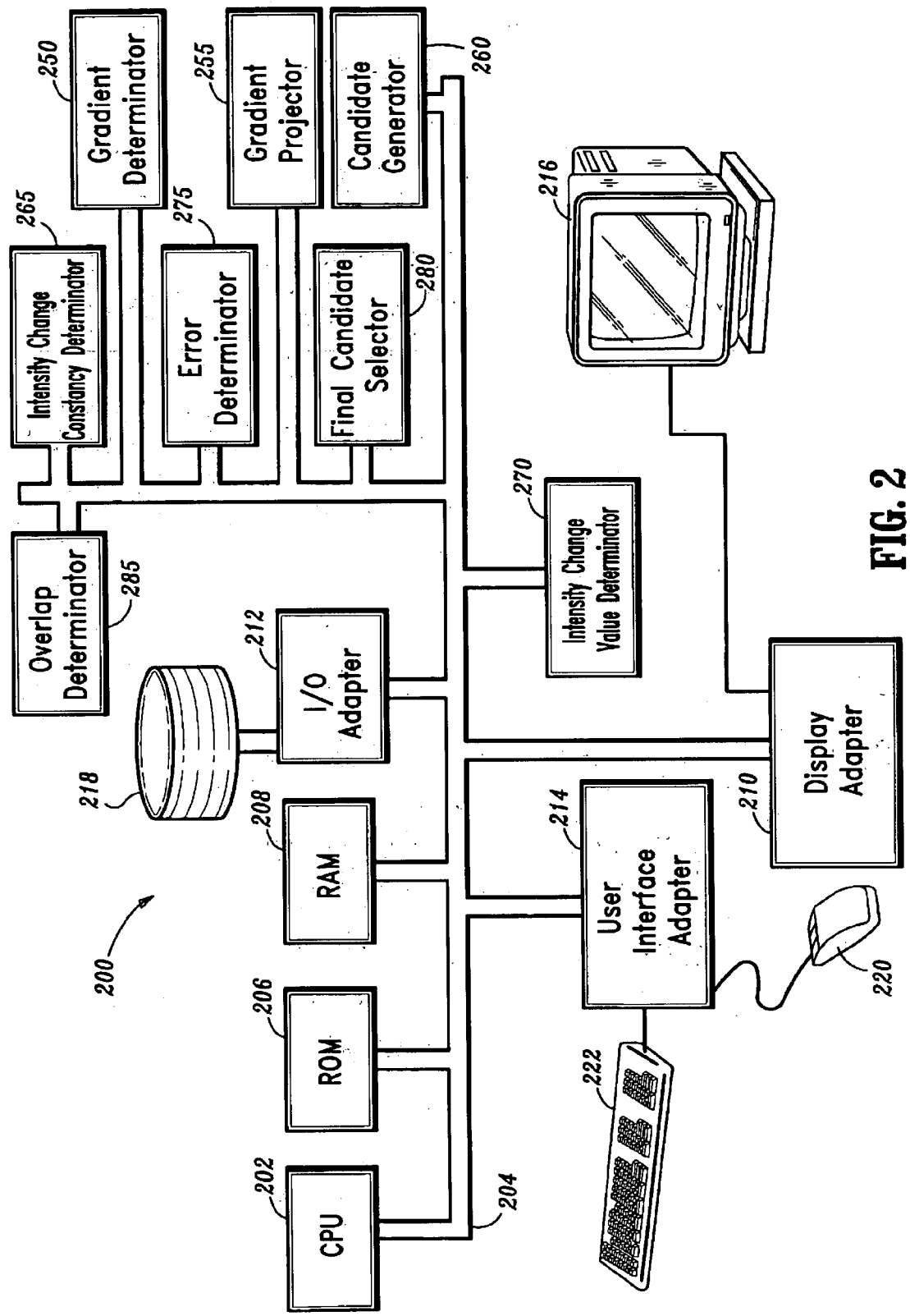
FIG. 2 is a block diagram of a system 100 for automatic Computed Radiography (CR) image composition by white band detection and consistency checking, according to an illustrative embodiment of the invention.

FIG. 2 is a block diagram of a system 100 for automatic Computed Radiography (CR) image composition by white band detection and consistency checking, according to an illustrative embodiment of the invention. The system 200 includes at least one processor (CPU) 202 operatively coupled to other components via a system bus 204. A read only memory (ROM) 206, a random access memory (RAM) 208, a display adapter 210, an I/O adapter 212, and a user interface adapter 214 are operatively coupled to the system bus 204.

A display device 216 is operatively coupled to the system bus 204 by the display adapter 210. A disk storage device (e.g., a magnetic or optical disk storage device) 218 is operatively coupled to the system bus 204 by the I/O adapter 212.

A mouse 220 and a keyboard 222 are operatively coupled to the system bus 204 by the user interface adapter 214.

A gradient determinator 250, a gradient projector 255, a candidate generator 260, an intensity change constancy determinator 265, an intensity change value determinator 270, and error determinator 275, a final candidate selector 280, and an overlap determinator 285 are also coupled to the system bus 204. The preceding elements are described in detail hereinbelow.

The system 200 may also include a digitizer 226 operatively coupled to system bus 204 by user interface adapter 214 for digitizing CR images. Alternatively, digitizer 226 may be omitted, in which case digital CR images may be input to system 200 from a network via a communications adapter 228 operatively coupled to system bus 204.

A general description of the present invention will now be provided with respect to FIG. 3 to introduce the reader to the concepts of the invention. Subsequently, a more detailed description of various aspects of the invention will be provided with respect to FIG. 4.

Figure 1:
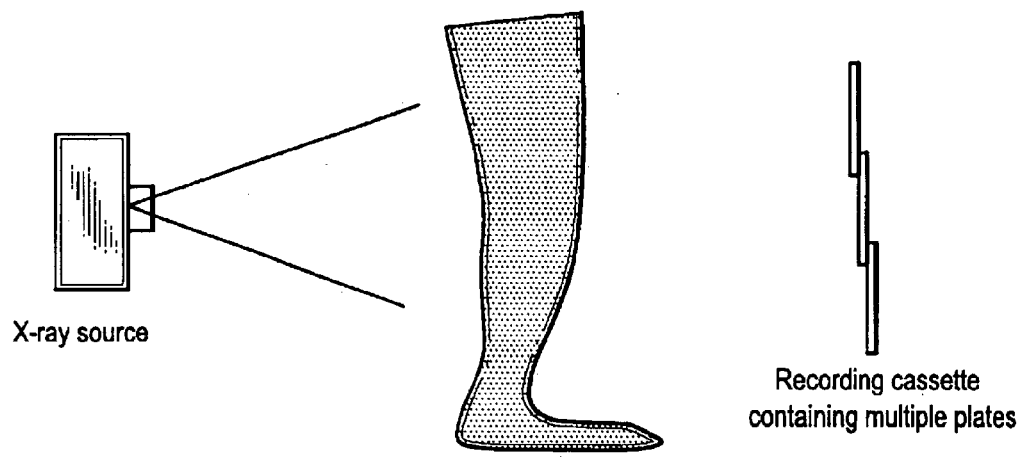
FIG. 1 is a diagram illustrating a simplified view of a Computed Radiography (CR) image acquisition, according to the prior art.
Figure 3A:
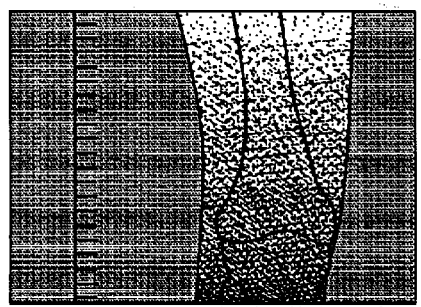
FIGS. 3A and 3B are diagrams respectively illustrating first and second images respectively having an overlap region at the bottom and top thereof, the overlap region in the second image being brighter than the lower part of the second image.
Figure 3B:
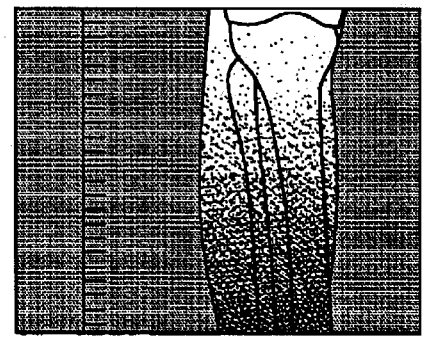

It has been observed that when two image plates overlap, the overlap region on the rear image plate (when viewed from the x-ray source) has a brighter image intensity. This brighter region is referred to herein as the "white band". FIGS. 3A and 3B are diagrams respectively illustrating first and second images respectively having an overlap region at the bottom and top thereof, the overlap region in the second image being brighter than the lower part of the second image. Note that in another configuration, wherein the image recording cassettes are put in a different order than in FIG. 1, i.e., from bottom to top instead of from top to bottom, the white band will appear at the bottom of the upper image.

Irrespective of the configuration, if the line of intensity transition between the white band and the rest of the image could be reliably detected, then the two images can then be combined as a mosaic to provide a larger composed image. The line of this intensity transition is referred to herein as the "white band edge". The present invention is primarily focused on the detection of the white band edge.

Figure 4:
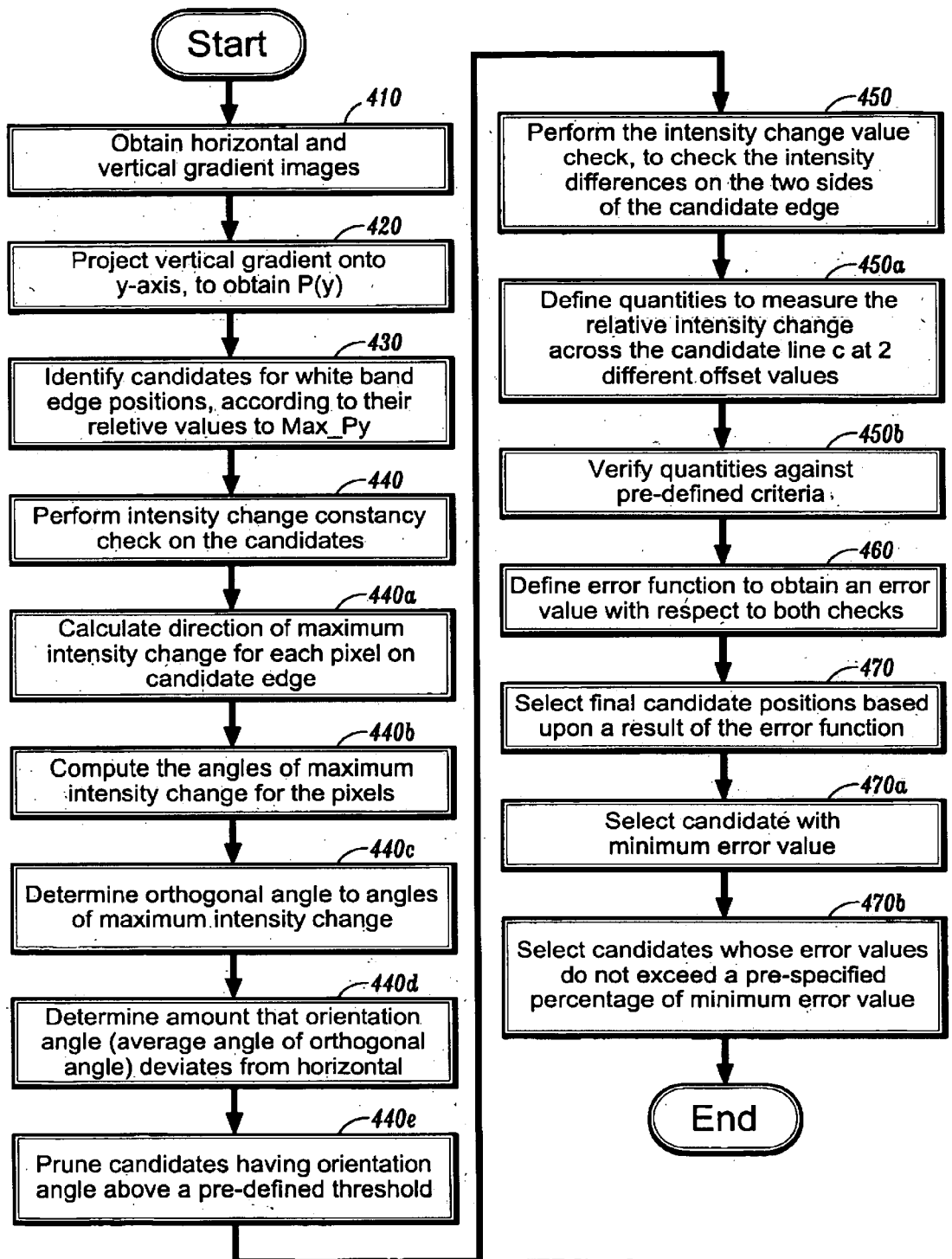
FIG. 4 is a flow diagram illustrating a method for detecting white band edges in Computed Radiography (CR) images, according to an illustrative embodiment of the present invention.
Figure 5A:
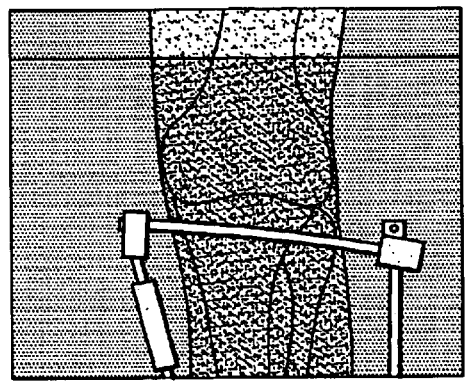
FIGS. 5A–D are diagrams respectively illustrating an original, Computed Radiography (CR) intensity image, a corresponding vertical gradient image, and a corresponding y-axis projection, according to an illustrative embodiment of the present invention.
Figure 5B:
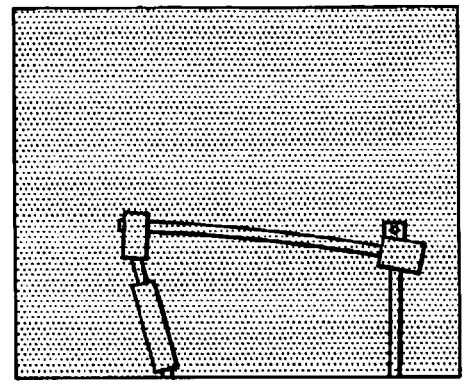
Figure 5C:
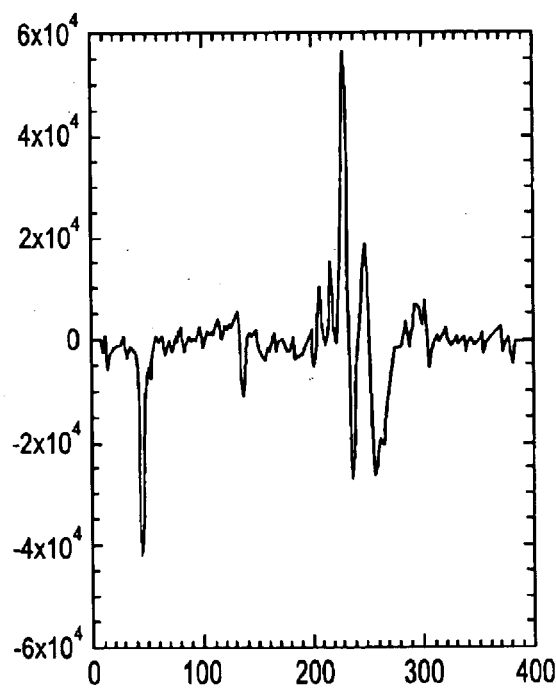
Figure 5D:
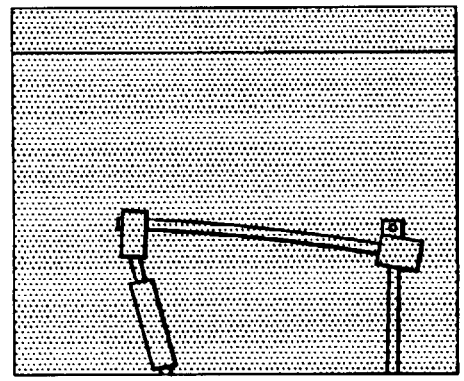

FIG. 4 is a flow diagram illustrating a method for detecting white band edges in Computed Radiography (CR) images, according to an illustrative embodiment of the present invention. It is to be appreciated that the method of FIG. 4 is applied to each image independently. After the white band edge detection, a cross-correlation method is used to make final decisions about how the images should be aligned, as described, for example, in FIG. 6 hereinbelow.

Suppose I (x,y) represents a digitized Computed Radiography (CR) image. Derivative operations are first applied to the CR image I (x,y) by the gradient determinator 250 to obtain corresponding horizontal and vertical gradient images $I_x$ (x,y) and $I_y$ (x,y), respectively (step 410). The vertical gradient image is projected onto the y-axis of the CR image I (x,y) by the gradient projector 255 (step 420) according to the following equation:

$$P(y) = \sum_x I_y(x, y)$$

Since the white band edge is nearly horizontal, the pixels on the white band edge will project to about the same position on the y-axis. FIGS. 5A–D are diagrams respectively illustrating an original, Computed Radiography (CR) intensity image, a corresponding vertical gradient image, and a corresponding y-axis projection, according to an illustrative embodiment of the present invention. It can be seen that at the white band edge, the vertical gradient image shows a darker line, indicating an intensity transition from bright to dark (an upper white band). The origin of the coordinate system is at the upper-left corner of the image. For a lower white band, the transition line will be bright, i.e., a transition from dark to white. The white band edge of FIG. 5B generates a negative peak in the projection curve P(y), as shown between 40 and 50 on the x-coordinates of FIG. 6C.

Next, candidates for the white band edge positions are identified by the candidate generator 260 (step 430) according to their relative value to the absolute maximum value Max_Py:

$$\text{Max\_Py} = \max_y |P(y)|$$

All peaks (both positive and negative) whose absolute values are above some pre-specified percentage of Max_Py are considered. For illustrative purposes, this percentage value is set at 40% herein. Of course, other pre-specified percentage values of Max_Py may be employed. That is, given the teachings of the present invention provided herein, one of ordinary skill in the related art will contemplate a pre-specified percentage value of Max_Py equal to 40% as well as various other pre-specified percentage values of Max_Py, while maintaining the spirit and scope of the present invention.

For all the candidate positions, an "intensity change constancy-check" is performed by the intensity change constancy determinator 265 (step 440). The intensity change constancy-check identifies the candidate edge positions having orientation angles less than a pre-defined threshold angle with respect to the horizontal, the orientation angles being orthogonal with respect to angles of maximum intensity change for pixels on the candidate edge positions.

The intensity change constancy-check is performed by first calculating the direction of maximum intensity change for each pixel on the candidate edge in the original image (step 440a). Suppose $\Omega\{c|c=1,2,\ldots,N_c\}$ is the set of indices for the candidate edges, with y-coordinates at $\{Y_c|c=1,2,\ldots,N_c\}$ in the original image. Then, the angles of maximum intensity change for pixels on line c are computed (step 440b) as $$R_c(x)=\arctan(I_y(x,y_c),I_x(x,y_c)); x \in D_c, c \in \Omega$$

where $D_c$ is the set of points whose vertical gradient are non-zero, which is used to exclude over-saturated or under-exposed (black) pixels. Denote/determine the orthogonal angle to $R_c(x)$ by $R^\perp_c(x)$ (step 440c). Then, the intensity change consistency is measured by how much the average angle of $R^\perp_c(x)$ over x is deviated from being horizontal (step 440d). This average angle represents the orientation angle of the candidate edge, and is denoted by $A_c$:

$$A_c = \sum_{x \in D_c} R^\perp_c(x)/|D_c|$$

where $|D_c|$ is the number of elements in $D_c$. A pre-defined threshold is used to prune the candidates (step 440e): candidates with $A_c$ above the pre-defined threshold are excluded from being further considered and are rejected at this stage. This threshold value is chosen as 30 degrees in the illustrative embodiment. Of course, other values for the pre-defined threshold may be employed. That is, given the teachings of the present invention provided herein, one of ordinary skill in the related art will contemplate a pre-defined threshold value of 30 degrees for the average angle of $R^\perp_c(x)$ as well as other pre-defined threshold values for the average angle of $R^\perp_c(x)$, while maintaining the spirit and scope of the present invention. The set $\Omega$ is updated accordingly to reflect the result of this pruning.

Candidates that pass the intensity change consistency check are subject to the "intensity change value check" by the intensity change value determinator 270 (step 450), which explicitly checks the intensity value differences on the two sides of the candidate edge. Define:

$$\Delta I_{1,c} = \frac{\sum_{x \in D_c} |I(x, y_c + \delta_1) - I(x, y_c - \delta_1)|}{\min\left\{\sum_{x \in D_c} I(x, y_c + \delta_1), \sum_{x \in D_c} I(x, y_c - \delta_1)\right\}} \quad c \in \Omega$$

$$\Delta I_{2,c} = \frac{\sum_{x \in D_c} |I(x, y_c + \delta_2) - I(x, y_c - \delta_2)|}{\min\left\{\sum_{x \in D_c} I(x, y_c + \delta_2), \sum_{x \in D_c} I(x, y_c - \delta_2)\right\}} \quad c \in \Omega$$

where $\delta_1$ and $\delta_2$ are pre-defined offset values, which are set to 1 and 2 pixels, respectively, in the illustrative embodiment (step 450a). The quantities $\Delta I_{1,c}$ and $\Delta I_{2,c}$ measure the relative intensity change across the candidate line c at two different offset values. The criteria for passing the intensity change value-check are applied (step 450b) as follows:

$$\Delta I_{min,c} \stackrel{def}{=} \min(\Delta I_{1,c}, \Delta I_{2,c}) > \Delta_{min}$$

$$\Delta I_{max,c} \stackrel{def}{=} \max(\Delta I_{1,c}, \Delta I_{2,c}) < \Delta_{max}$$

$$\gamma \stackrel{def}{=} \min(\Delta I_{1,c}, \Delta I_{2,c}) / \max(\Delta I_{1,c}, \Delta I_{2,c}) > \gamma_{min}$$

The first two inequalities indicate that the intensity change across the white band edge should be at least $\Delta_{min}$, but should not exceed $\Delta_{max}$. The third inequality requires that the two measurements should not differentiate by a pre-defined ratio value. The values of $\Delta_{min}$, $\Delta_{max}$, and $\gamma_{min}$ are chosen as 0.05, 1.00, and 0.60, respectively, in the illustrative embodiment.

There might be multiple candidates remaining after the intensity change consistency-check (in step 440) and intensity change value-check (in step 450). An error function is then defined by the error determinator 275 with respect to the intensity change consistency-check and the intensity change value-check, to measure how well each candidate passes both checks (step 460):

$$E_c = A_c(\Delta_{max} - \Delta I_{max,c})(2-\gamma)$$

This value gets smaller when $\Delta_c$ becomes smaller, and also gets smaller when $\Delta I_{max,c}$ becomes larger. If $\gamma$, which measures the difference between two intensity change measurements, is 1 (indicating no difference), then $E_c$ does not get changed; otherwise, $E_c$ gets magnified by $(2-\gamma)$.

From the remaining candidates, final candidate edge positions are selected by the final candidate selector 280 based upon a result of the error function of step 460 (step 470).

According to one illustrative embodiment of the present invention, from the remaining candidates, the one with the minimum error $E_{min}$ is first selected (step 470a). Then, the candidates whose error measures $\{E_c\}$ do not exceed a pre-specified percentage value of $E_{min}$ are also kept (step 470b). This percentage value is set as 50% in the illustrative embodiment. Of course, other pre-specified percentage values of $E_{min}$ may be employed. That is, given the teachings of the present invention provided herein, one of ordinary skill in the related art will contemplate a pre-specified percentage value of $E_{min}$ equal to 50% as well as various other pre-specified percentage values of $E_{min}$, while maintaining the spirit and scope of the present invention. The sign information of $P(y_c)$ for candidate edge c indicates whether the detected white band edge corresponds to an upper white band or a lower white band. Most of the time, the number of candidates white band edges after running the whole pruning procedure is one. It is to be appreciated that the steps described above are performed to provide final candidates for the method of FIG. 6.

Figure 6:
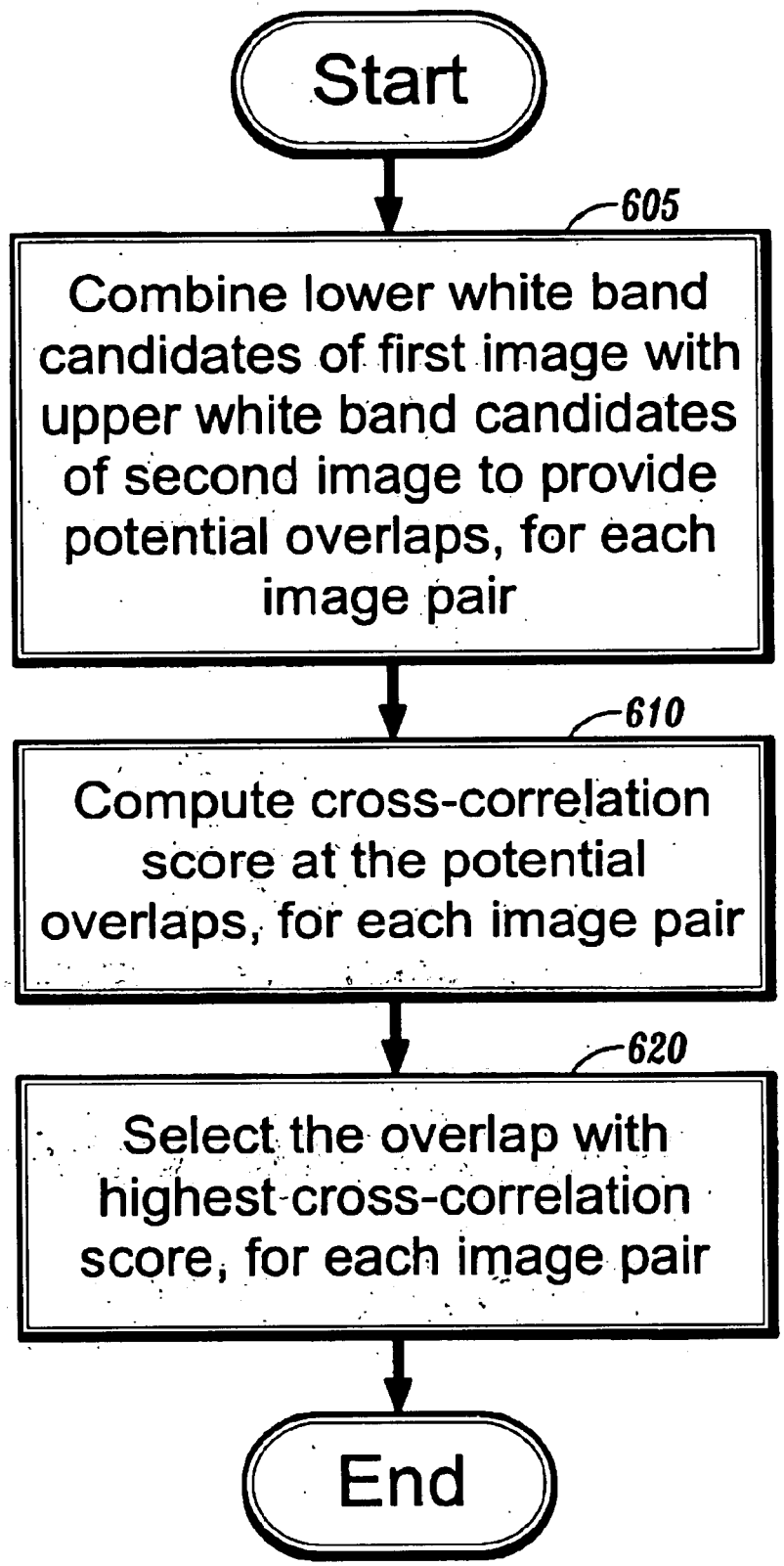
FIG. 6 is a flow diagram illustrating a method for cross-correlating two Computed Radiography (CR) images to align the two CR images, according to an illustrative embodiment of the present invention.

FIG. 6 is a flow diagram illustrating a method for cross-correlating two Computed Radiography (CR) images to align the two CR images, according to an illustrative embodiment of the present invention. To compose a mosaic image, images are considered pair-wise sequentially. For each image pair, the lower white band candidates of the first image and the upper white band candidates of the second image are combined by the overlap determinator 285 (step 605) to provide potential overlaps between the image pair. Cross-correlation scores for the potential overlaps are computed by the overlap determinator 285 (step 610). The potential overlap with the highest correlation score is selected by the overlap determinator 285 as the final choice for each image pair (step 620). Since there could be slight x-directional shift between image-recording cassettes, this x-directional shift is also considered at the same time in the correlation. If the number of candidate white band edges for an image pair is zero, the correlation computation is done on all admissible overlaps.

FIGS. 7A and 7B are diagrams illustrating an example of mosaic composition from 5 individual images, according to an illustrative embodiment of the present invention. In particular, FIG. 7A illustrates the 5 individual images, and FIG. 7B illustrates the mosaic resulting from the combination of the 5 individual images.

Although the illustrative embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the invention as defined by the appended claims.

What is claimed is:

1. A method for automatic Computed Radiography (CR) image composition by white band detection and consistency rechecking, comprising the steps of:

receiving an original CR image pair for composition;

for each image in the original CR image pair,
generating a horizontal gradient image and a vertical gradient image;
projecting the vertical gradient image onto a y-axis of the each image to obtain a y-axis projection;
identifying candidate edge positions from among at least two white band edge positions according to a relative value of each of the at least two white band edge positions with respect to a percentage value of an absolute maximum value of the y-axis projection;
determining an intensity change constancy of the candidate edge positions to identify the candidate edge positions having orientation angles less than a pre-defined threshold angle with respect to a horizontal, the orientation angles being orthogonal with respect to angles of maximum intensity change for pixels on the candidate edge positions;
determining an intensity change value to verify intensity value differences on two sides of the candidate edge positions with respect to predefined criteria;
defining an error function to respectively obtain an error value for each of the candidate edge positions with respect to the intensity change constancy and the intensity change value;
selecting the candidate edge positions having the error value below a pre-specified threshold;
computing a cross-correlation score for the selected candidate edge positions, by comparing a consistency of the selected candidate edge positions against image data corresponding to the original image pair; and
identifying a final overlap for the original image pair, based upon the cross-correlation score.

2. The method according to claim 1, wherein I (x,y) represents the each image in the original CR image pair, $I_x$ (x,y) and $I_y$ (x,y) respectively represent the horizontal gradient image and the vertical gradient image, and the y-axis projection is equal to $$P(y) = \sum_x I_y(x, y).$$

3. The method according to claim 1, wherein the absolute maximum value of the y-axis projection is equal to $$\text{Max\_Py} = \max_y |P(y)|.$$

4. The method according to claim 1, wherein $\Omega = \{c | c = 1, 2, \ldots, N_c\}$ represents a set of indices for the candidate edge positions having y-coordinates at $\{Y_c | c = 1, 2, \ldots, N_c\}$ in the each image, the angles of maximum intensity change for the pixels on a candidate edge position c from among the candidate edge positions are $R_c(x) = \arctan(I_y(x,y_c), I_x(x,y_c))$; $x \in D_c$, $c \in \Omega$, where $D_c$ is a set of points having a vertical gradient that is non-zero.

5. The method according to clam 4, wherein the set of points $D_c$ is used to exclude over-saturated and under-exposed pixels.

6. The method according to claim 4, wherein an orthogonal angle to $R_c(x)$ is $R^\perp_c(x)$, an average angle of $R^\perp_c(x)$ represents an orientation angle of the candidate edge position c, and is equal to $A_c$, $$A_c = \sum_{x \in D_c} R^\perp_c(x)/|D_c|,$$

and $|D_c|$ is a number of elements in the set of points $D_c$.

7. The method according to claim 1, further comprising the step of excluding any of the candidate edge positions having an average angle below a pre-determined threshold from further consideration.

8. The method according to claim 1, wherein said step of determining the intensity change constancy comprises the steps of:

for each of the candidate edge positions,
    determining a direction of maximum intensity change for each of pixels on the each of the candidate edge positions;
    determining an orthogonal angle with respect to the direction of maximum intensity change;
    calculating a deviation of an orientation angle, measured as an average angle of the orthogonal angle, from the horizontal; and
    identifying the candidate edge positions having the deviation less than the pre-defined threshold.

9. The method according to claim 1, wherein said step of determining the intensity change value comprises the steps of:

measuring a relative intensity change across a candidate edge position c at two different, pre-defined offset values; and
verifying that the relative intensity change satisfies the pre-defined criteria.

10. The method according to claim 9, wherein said measuring step comprises the step of determining $$\Delta I_{1,c} = \frac{\sum_{x \in D_c} |I(x, y_c + \delta_1) - I(x, y_c - \delta_1)|}{\min\left\{\sum_{x \in D_c} I(x, y_c + \delta_1), \sum_{x \in D_c} I(x, y_c - \delta_1)\right\}} \quad c \in \Omega$$

$$\Delta I_{2,c} = \frac{\sum_{x \in D_c} |I(x, y_c + \delta_2) - I(x, y_c - \delta_2)|}{\min\left\{\sum_{x \in D_c} I(x, y_c + \delta_2), \sum_{x \in D_c} I(x, y_c - \delta_2)\right\}} \quad c \in \Omega,$$

where $\delta_1$ and $\delta_2$ are the two different, pre-defined offset values, and $\Delta I_{1,c}$ and $\Delta I_{2,c}$ indicate the relative intensity change across the candidate edge position c at the two different, pre-defined offset values.

11. The method according to claim 10, wherein said verifying step comprises the step of verifying $$\Delta I_{\min,c} \stackrel{def}{=} \min(\Delta I_{1,c}, \Delta I_{2,c}) > \Delta_{\min};$$

$$\Delta I_{\max,c} \stackrel{def}{=} \max(\Delta I_{1,c}, \Delta I_{2,c}) < \Delta_{\max}; \text{ and}$$

$$\gamma \stackrel{def}{=} \min(\Delta I_{1,c}, \Delta I_{2,c})/\max(\Delta I_{1,c}, \Delta I_{2,c}) > \gamma_{\min}.$$

12. The method according to claim 1, wherein said selecting step comprises the step of selecting a candidate edge position having a smallest error value.

13. The method according to claim 12, wherein said selecting step further comprises the step of selecting any remaining candidate edge positions having the error value that is less than a pre-specified percentage of the smallest error value.

14. A system for automatic Computed Radiography (CR) image composition by white band detection and consistency rechecking, comprising:

means for receiving an original CR image pair for composition;
a gradient determinator for generating a horizontal gradient image and a vertical gradient image, for each image in the original CR image pair;
a gradient projector for projecting, for the each image, the vertical gradient image onto a y-axis of the each image to obtain a y-axis projection;
a candidate generator for identifying, for the each image, candidate edge positions from among at least two white band edge positions according to a relative value of each of the at least two white band edge positions with respect to a percentage value of an absolute maximum value of the y-axis projection;
an intensity change constancy determinator for determining an intensity change constancy of the candidate edge positions for the each image, to identify the candidate edge positions having orientation angles less than a pre-defined threshold angle with respect to a horizontal, the orientation angles being orthogonal with respect to angles of maximum intensity change for pixels on the candidate edge positions;
an intensity change value determinator for determining an intensity change value to verify intensity value differences on two sides of the candidate edge positions, for the each image with respect to predefined criteria;
an error determinator for defining an error function to respectively obtain an error value for each of the candidate edge positions for the each image with respect to the intensity change constancy and the intensity change value, and for selecting the candidate edge positions, for the each image, having the error value below a pre-specified threshold; and an overlap determinator for computing a cross-correlation score for the selected candidate edge positions for the each image by comparing a consistency of the selected candidate edge positions against image data corresponding to the original image pair, and for identifying a final overlap for the original image pair, based upon the cross-correlation score.

15. The system according to claim 14, wherein I (x,y) represents the each image in the original CR image pair, $I_x$ (x,y) and $I_y$ (x,y) respectively represent the horizontal gradient image and the vertical gradient image, and the y-axis projection is equal to $$P(y) = \sum_x I_y(x, y).$$

16. The system according to claim 14, wherein the absolute maximum value of the y-axis projection is equal to $$\text{Max\_Py} = \max_y |P(y)|.$$

17. The system according to claim 14, wherein $\Omega = \{c | c=1,2,\ldots, N_c\}$ represents a set of indices for the candidate edge positions having y-coordinates at $\{Y_c | c=1,2, \ldots, N_c\}$ in the each image, the angles of maximum intensity change for the pixels on a candidate edge position c from among the candidate edge positions are $R_c(x) = \arctan(I_y(x,y_c), I_x(x,y_c))$; $x \in D_c, c \in \Omega$, where $D_c$ is a set of points having a vertical gradient that is non-zero.

18. The system according to clam 17, wherein the set of points $D_c$ is used to exclude over-saturated and under-exposed pixels.

19. The system according to claim 17, wherein an orthogonal angle to $R_c(x)$ is $R^\perp_c(x)$, an average angle of $R^\perp_c(x)$ represents an orientation angle of the candidate edge position c, and is equal to $A_c$, $$A_c = \sum_{x \in D_c} R^\perp_c(x)/|D_c|,$$

and $|D_c|$ is a number of elements in the set of points $D_c$.

20. The system according to claim 14, wherein said intensity change constancy determinator excludes any of the candidate edge positions having an average angle below a pre-determined threshold from further consideration.

21. The system according to claim 14, wherein said intensity change constancy determinator, for each of the candidate edge positions, determines a direction of maximum intensity change for each of pixels on the each of the candidate edge positions, determines an orthogonal angle with respect to the direction of maximum intensity change, calculates a deviation of an orientation angle, measured as an average angle of the orthogonal angle, from the horizontal, and identifies the candidate edge positions having the deviation less than the pre-defined threshold.

22. The system according to claim 14, wherein said intensity change value determinator measures a relative intensity change across a candidate edge position c at two different, pre-defined offset values, and verifies that the relative intensity change satisfies the pre-defined criteria.

23. The system according to claim 22, wherein said intensity change value determinator measures the relative intensity change across the candidate edge position c at the two different, pre-defined offset values by determining $$\Delta I_{1,c} = \frac{\sum_{x \in D_c} |I(x, y_c + \delta_1) - I(x, y_c - \delta_1)|}{\min\left\{\sum_{x \in D_c} I(x, y_c + \delta_1), \sum_{x \in D_c} I(x, y_c - \delta_1)\right\}} \quad c \in \Omega$$

$$\Delta I_{2,c} = \frac{\sum_{x \in D_c} |I(x, y_c + \delta_2) - I(x, y_c - \delta_2)|}{\min\left\{\sum_{x \in D_c} I(x, y_c + \delta_2), \sum_{x \in D_c} I(x, y_c - \delta_2)\right\}} \quad c \in \Omega,$$

where $\delta_1$ and $\delta_2$ are the two different, pre-defined offset values, and $\Delta I_{1,c}$ and $\Delta I_{2,c}$ indicate the relative intensity change across the candidate edge position c at the two different, pre-defined offset values.

24. The system according to claim 23, wherein said intensity change value determinator verifies that the relative intensity change satisfies the pre-defined criteria by verifying $$\Delta I_{\min,c} \stackrel{def}{=} \min(\Delta I_{1,c}, \Delta I_{2,c}) > \Delta_{\min};$$

$$\Delta I_{\max,c} \stackrel{def}{=} \max(\Delta I_{1,c}, \Delta I_{2,c}) < \Delta_{\max}; \text{ and}$$

$$\gamma \stackrel{def}{=} \min(\Delta I_{1,c}, \Delta I_{2,c})/\max(\Delta I_{1,c}, \Delta I_{2,c}) > \gamma_{\min}.$$

25. The system according to claim 14, wherein said error determinator selects a candidate edge position having a smallest error value.

26. The system according to claim 25, wherein said error determinator further selects any remaining candidate edge positions having the error value that is less than a pre-specified percentage of the smallest error value.

* * * * *